(12) United States Patent
LeGette

(10) Patent No.: US 9,205,160 B1
(45) Date of Patent: Dec. 8, 2015

(54) HORTICULTURAL PRUNING SAW DISINFECTING TUBE AND METHOD

(76) Inventor: James LeGette, Davie, FL (US)

( * ) Notice: Subject to any disclaimer, the term of this patent is extended or adjusted under 35 U.S.C. 154(b) by 16 days.

(21) Appl. No.: 13/541,073

(22) Filed: Jul. 3, 2012

Related U.S. Application Data

(60) Provisional application No. 61/507,431, filed on Jul. 13, 2011.

(51) Int. Cl.
*A61L 2/18* (2006.01)

(52) U.S. Cl.
CPC ........................................ *A61L 2/18* (2013.01)

(58) Field of Classification Search
USPC ............. 422/292; 30/515, 151; 206/317, 207, 206/349; 220/735; 446/15
See application file for complete search history.

(56) References Cited

U.S. PATENT DOCUMENTS

| | | | | |
|---|---|---|---|---|
| 1,598,443 | A * | 8/1926 | Horan | 206/207 |
| 4,601,081 | A * | 7/1986 | Sutton et al. | 15/104.94 |
| 5,582,333 | A * | 12/1996 | Bennett | 222/546 |
| 6,135,842 | A * | 10/2000 | LaFata | 446/15 |
| 6,554,156 | B1 * | 4/2003 | Chong | 221/63 |
| 7,066,675 | B1 * | 6/2006 | Miller | 401/126 |
| 2006/0118557 | A1 * | 6/2006 | Tack et al. | 220/259.1 |
| 2006/0266761 | A1 * | 11/2006 | Rhea | 221/45 |
| 2007/0145059 | A1 * | 6/2007 | Ogura et al. | 220/723 |

OTHER PUBLICATIONS

Definition of "cylinder" Webster's Colelge Dictionary 2010.*
Definition of "surround" The American Heritage Dictionary. 2009.*
"Bubble Formulae" retrieved from Internet Archive Wayback Machine Capture on Aug. 3, 2009.*
"Plastic Bottle" retrieved from Wikipedia revision histroy as appeared on Jul. 4, 2010.*
"Pine Sol". The Clorox Company. Capture from May 15, 2015. https://www.pinesol.com/products/original-pine-cleaner/.*

* cited by examiner

*Primary Examiner* — Sean E Conley
*Assistant Examiner* — Donald Spamer
(74) *Attorney, Agent, or Firm* — Daniel S. Polley, P.A.

(57) ABSTRACT

A pruning saw blade disinfecting assembly comprising a cylinder with a removable lid at an open end. The other end of the cylinder is closed. A slit or other opening is provided at the top of the lid to allow the pruning saw blade to be inserted therethrough and into the interior area of the cylinder. The cylinder is preferably filled with a disinfecting solution. When the saw blade is inserted into the tube through the slit opening in the top of the removable lid, the saw blade comes into contact with the disinfecting solution. In a proper insertion position, the handle of the pruning saw remains on the outside and a significant majority of the blade portion of the pruning saw is submerged within the disinfecting solution. After it has been submerged for a sufficient period of time, the saw is pulled out and is ready for use.

4 Claims, 1 Drawing Sheet

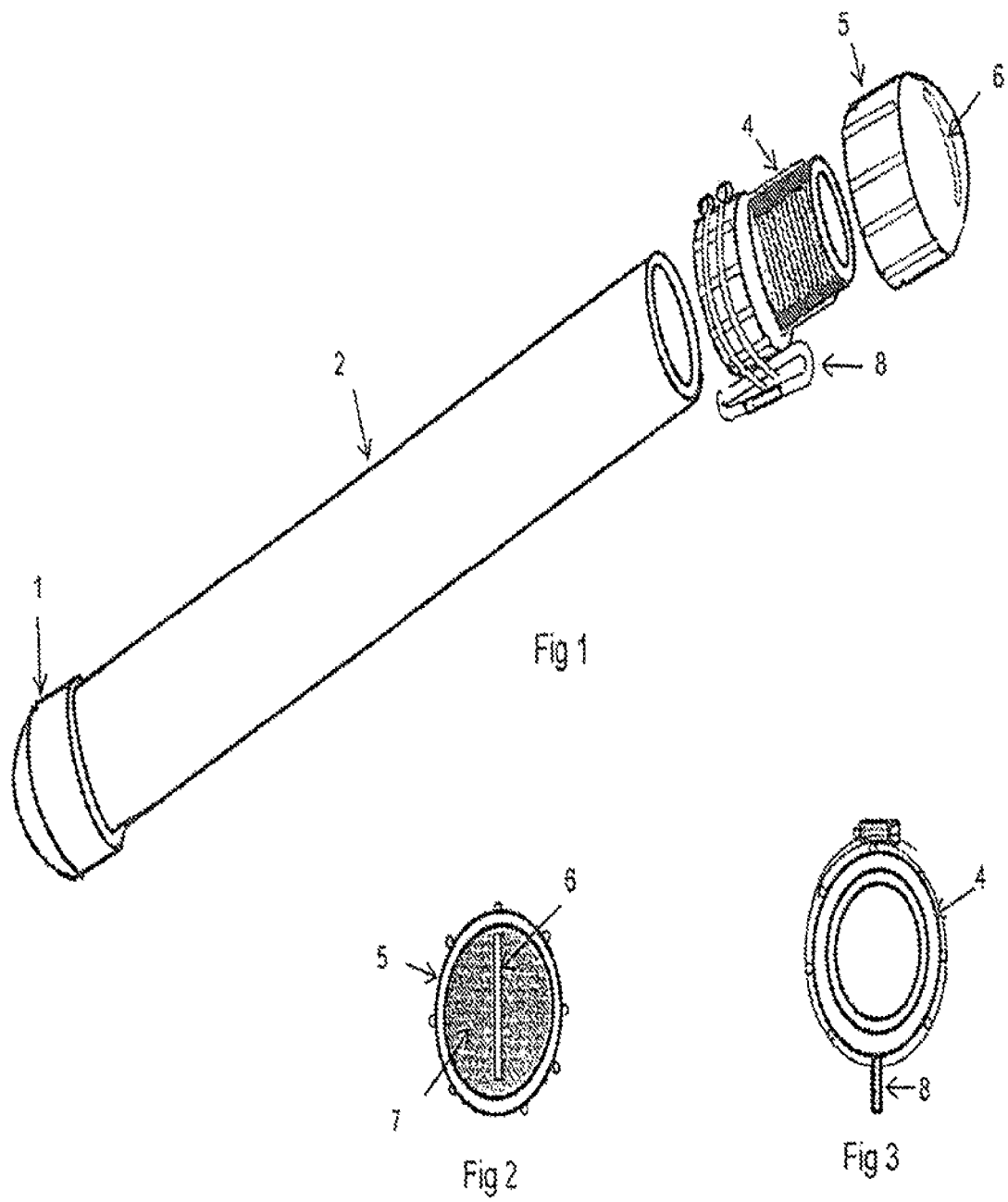

HORTICULTURAL PRUNING SAW DISINFECTING TUBE AND METHOD

This application claims the benefit of and priority to U.S. Application Ser. No. 61/507,431 filed on Jul. 13, 2011, which is incorporated by reference in its entirety.

FIELD OF THE INVENTION

The present invention relates generally to pruning saws and particularly to a device and method for disinfecting pruning saws.

BACKGROUND OF THE INVENTION

In the field, an arborist after pruning a tree with his or her pruning saw typically places the saw back into a sheath or other saw holder connected to the arborist's belt. The tree just pruned may be infected with a disease, which may become disposed on the saw blade. If the arborist is unaware of such fact, the disease may remain on the saw blade when the arborist begins to prune a next tree. If the next tree is healthy, the use of the saw blade containing the disease by the arborist to prune such tree may cause the healthy tree to unknowingly become infected with the disease. It is to overcoming or reducing the occurrences of unintentionally infecting healthy trees with a disease during pruning that the present invention is directed.

SUMMARY OF THE INVENTION

The present invention device provides the arborists and other individuals with an efficient and easy to use device for achieving pruning saw sanitation. Used properly, the present invention device disinfects most straight blade hand landscaping pruning saws.

The present invention generally comprises a cylinder with a removable lid and in a preferred embodiment can comprise an elongated PVC cylinder having a closed first end and an open second end with a removable lid secured at the open second end by any conventional means, such as, but not limited to, a snug fitting between the lid and the open end or through a mating thread configuration consisting of external threads at the open end of the cylinder and internal threads on the screw lid.

A slit or other opening sufficient in size is provided at the top of the lid to allow the pruning saw blade to be inserted therethrough and into the interior area of the cylinder. The cylinder is preferably filled with a horticultural disinfecting solution. When the saw blade is inserted into the tube through the slit opening in the top of the removable lid, the saw blade comes into contact with the disinfecting solution. In a proper insertion position, the handle of the pruning saw remains on the outside and is abutting or adjacent the top of the lid and a significant majority of the blade portion of the pruning saw is submerged within the disinfecting solution. Once the saw has been submerged for a sufficient period of time (i.e. long enough to allow the disinfecting solution to kill any disease, bacteria, germs, etc.), it can be pulled out and is ready for use in connection with pruning the next tree.

A carabineer or other attachment mechanism can be secured to the cylinder to facilitate attachment of the cylinder to the user's hip area by attachment to the user's tool belt or other belt or belt loop. In this position, the present invention is easy to use and readily accessible. The connection of the cylinder in this manner also permits it to remain in an upright position to help prevent the disinfecting solution from leaking out of the slit opening in the lid.

As an alternative attachment mechanism in lieu of the carabineer, a relatively small hole (i.e. ¼", etc.), can be drilled near the top end of the cylinder and an eyebolt or other hook mechanism can be inserted therein to provide an attachment point to hang or otherwise secure the cylinder to a work belt, tool belt or other belt being worn by the user.

It is also preferred, that the disinfecting solution is changed periodically relative to the frequency of use of the present invention.

BRIEF DESCRIPTION OF THE DRAWINGS

FIG. 1 is an exploded perspective view of one embodiment for the pruning saw disinfector in accordance with the present invention;

FIG. 2 is a bottom view of one embodiment for the removable lid member of the pruning saw disinfector of FIG. 1; and FIG. 3 is a bottom view of a tube connector or manifold member of the pruning saw disinfector of FIG. 1.

DETAILED DESCRIPTION OF THE INVENTION

As seen in the drawings an efficient and easy to use device for achieving pruning saw sanitation is provided and generally comprises an elongated tube 2 having a closed end 1 and an opposite open end. Tube 2 can be constructed closed at end 1 or a closed cover member can be secured at end 1 to close or seal end 1 in order to prevent fluids within tube 2 from escaping out at end 1. Where a cover member is provided it is preferably permanently secured to tube 2 at end 1. Used properly, the present invention device disinfects most straight blade hand pruning saws, though other saws, knives and tools can also be inserted within tube 2 in the field for sanitation purposes and are also considered within the scope of the invention.

A removable lid or cap 5 is preferably secured at the open end of tube 2. In one embodiment a tube connector or manifold member (FIGS. 1 and 3) can be secured at the open end of tube 2 and acts as the connection mechanism for securing lid 5 to tube 2. Though not considered limiting, the tube coupling/connector/manifold can be permanently secured to tube 2 at the open end. A post portion 4 of the tube coupling can contain a plurality of external threads for mating with internal threads contained on the inner sidewall of the removable lid 5. Removable lid 5 can be a screw lid that mates with the tube connector by mating the threads with each other. Alternatively, if no threads are provided, removable lid 5 can be snugly secured to post portion 4 of the tube coupling or if no tube coupling is provided, removable lid 5 can be snugly secured directly to the open end of tube 2. Lastly, where no tube coupling is provided, external threads can be provided on the outer surface at the open end of tube 2 which can mate with internal threads on the inner sidewall of removable lid 5.

It is also within the scope of the invention that tube 2, the cover at closed end 1 and the tube coupling can all be monolithically formed as a one-piece member or that the tube and cover or the tube and tube coupling can be monolithically formed as one-piece members. Though not preferred, it is also within the scope of the invention that lid 5 is also permanently secured and can also be monolithically formed with some or all of the above identified portions of the present invention device.

In a preferred embodiment tube 2, as well as the cover at closed end 1, the tube coupling and removable lid 5 can all be made from PVC, though such is not considered limiting and other materials may be used and are considered within the scope of the invention.

A slit, slot or other opening 6 sufficient in size is provided at the top of removable lid 5 to allow the pruning saw blade to be inserted therethrough and into the interior area of cylinder/tube 2. Cylinder 2 is preferably filled with a horticultural disinfecting solution. When the saw blade is inserted into tube 2 through slit opening 6 in the top of the removable lid 5, the saw blade comes into contact with the disinfecting solution. In a proper insertion position, the handle of the pruning saw remains on the outside and is abutting or adjacent the top of lid 5 and a significant majority of the blade portion of the pruning saw is submerged within the disinfecting solution. Once the saw has been submerged for a sufficient period of time (i.e. long enough to allow the disinfecting solution to kill any disease, bacteria, germs, etc.), it can be pulled out and is ready for use in connection with pruning the next tree. An insert 7, such as, but not limited to, a relatively thick rubber foam insert can be secured to the undersurface of the top of lid 5. Insert 7 surrounds slot 6 and can help to protect and guide the blade when it is inserted into the present invention device through slot 6.

Though not shown, any required sealing gaskets or washers, if any, may also be used in accordance with their normal known functions.

A carabineer or other attachment mechanism 8 can be secured to cylinder or the tube coupling to facilitate attachment of cylinder 2 to the user's hip area by attachment to the user's tool belt or other belt or belt loop. In this position, the present invention is easy to use and readily accessible. The connection of cylinder 2 in this manner also permits it to remain in an upright position to help prevent the disinfecting solution from leaking out of the slit opening 6 in the removable lid 5. Carabineer 8 can be secured by any conventional means and in a non-limiting embodiment is shown secured by at least one and preferably two or clamps, such as, but not limited to stainless steel pipe clamps.

As an alternative attachment mechanism in lieu of the carabineer, a relatively small hole (i.e. ¼", etc.), can be drilled near the top end of the cylinder and an eyebolt or other hook mechanism can be inserted therein to provide an attachment point to hang or otherwise secure the cylinder to a work belt, tool belt or other belt being worn by the user.

It is also preferred, that the disinfecting solution is changed periodically relative to the frequency of use of the present invention. In use, the pruning saw blade is inserted into slot 6 in the top of the present invention device for carrying the pruning saw and at the same time disinfecting the saw blade.

As seen in FIG. 1 slit 6 is unsurrounded on all sides of the outer exposed surface of lid 5. As seen in FIGS. 1 and 2, the slit can be elongated and/or substantially elliptical in shape with two essentially parallel opposite sides terminating at a rounded first end and a rounded second end.

For example purposes only, in one non-limiting embodiment, the cap at end 1 can be an about 2" diameter PVC cap that can be cemented to tube 2. Tube 2 can be an about 2" diameter by about 11" length Schedule 40 PVC pipe. The tube coupling can be an about 2" diameter Plaint end x threaded end PVC coupling that can be cemented to tube 2 and screwed onto lid 5. Lid 5 can be an about 2" diameter threaded PVC cap, that is removably screwed onto the tube coupling. Slot 6 in lid 5 can be about ³⁄₁₆" by about 1¾". The optional insert 7 can be an about ¾" thick foam rubber insert and the belt connector 8 can be an about 2½"carabineer.

In one non-limiting embodiment the disinfecting solution can be a combination of Pine Sol and water, however other solutions and combination of solutions and fluids can be used and all are considered within the scope of the invention.

All measurements, dimensions, amounts, values, percentages, materials, degrees, product configuration, product layout, component locations, sizes, orientations, belt attachment mechanisms, number of sections, number of components or items, etc. discussed above or shown in the Figures are merely by way of example and are not considered limiting and other measurements, dimensions, amounts, values, percentages, materials, degrees, product configuration, product layout, component locations, sizes, orientations, belt attachment mechanisms, number of sections, number of components or items, etc. can be chosen and used and all are considered within the scope of the invention.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function (s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. A combination pruning saw and pruning saw blade disinfecting assembly, comprising a hand held landscaping pruning saw having a straight blade and handle; and a pruning saw blade disinfecting assembly comprising:

an elongated cylindrical tube having a substantially circular cross sectional shape and a first closed end and an open second end, said tube has an internal area having a size sufficient to essentially house the blade portion of the straight blade hand held landscaping pruning saw while the handle remains externally located with respect to the tube;

a cap removably secured to said second end of said elongated tube, said cap having a dome-shaped outer end containing a slit on an external surface of said cap, said slit providing access to within the internal area of said elongated tube when said cap is secured to said elongated tube, said slit having a first side edge, a second side edge, a first end edge and a second end edge, wherein in use the first side edge, the second side edge, the first end edge and the second end edge of uncovered and said slit being unsurrounded on all sides are an outer exposed surface of said cap and having an elongated shape with two essentially parallel opposite sides terminating at a first end and a second end; and an amount of disinfecting solution in fluid form disposed within said internal area of said elongated tube.

2. The saw blade disinfecting assembly of claim 1 further comprising a tube coupling secured at said second end of said elongated tube, said tube coupling having a post portion, wherein said cap removably secured to said post portion.

3. The saw blade disinfecting assembly of claim 2 wherein said tube is adapted for securement to a belt worn by a user by an externally exposed carabineer, eyebolt or hook secured to the tube coupling near the second end of said tube and at a point with respect to the tube prior to reaching the cap.

4. The saw blade disinfecting assembly of claim 1 wherein said slit is sized large enough to receive a blade portion of only a single straight blade hand landscaping pruning saw but small enough so as not to receive a handle portion of the single straight blade hand landscaping pruning saw.

\* \* \* \* \*